United States Patent
Aupaix et al.

(10) Patent No.: US 6,811,723 B1
(45) Date of Patent: Nov. 2, 2004

(54) ORGANIC SOL AND SOLID COMPOUND BASED ON TITANIUM OXIDE AND AMPHIPHILIC COMPOUND AND PREPARATION METHODS

(75) Inventors: Nicole Aupaix, Plaisir (FR); Jean-Yves Chane-Ching, Eaubonne (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/913,883

(22) PCT Filed: Feb. 11, 2000

(86) PCT No.: PCT/FR00/00342

§ 371 (c)(1),
(2), (4) Date: Dec. 5, 2001

(87) PCT Pub. No.: WO00/49099

PCT Pub. Date: Aug. 24, 2000

(30) Foreign Application Priority Data

Feb. 17, 1999 (FR) .............................. 99 01940

(51) Int. Cl.$^7$ ............................. B01F 3/12; B01F 17/14; C09D 17/00; A61K 7/42
(52) U.S. Cl. ................. 252/363.5; 516/33; 106/287.19; 106/447; 423/611; 524/131; 524/497; 424/59
(58) Field of Search ....................... 516/33; 108/287.19, 108/447; 502/350; 423/611; 252/363.5; 524/131, 497; 424/59

(56) References Cited

U.S. PATENT DOCUMENTS

| | | | |
|---|---|---|---|
| 3,676,362 A | * | 7/1972 | Yates ........................... 516/33 |
| 5,397,391 A | * | 3/1995 | Stramel ....................... 106/447 |
| 5,599,529 A | * | 2/1997 | Cowie ........................... 424/59 |
| 5,605,652 A | * | 2/1997 | Tapley .......................... 424/59 |
| 5,821,027 A | * | 10/1998 | Landry-Coltrain et al. . 430/140 |
| 5,902,569 A | * | 5/1999 | Oshima et al. ................. 424/59 |
| 6,037,289 A | * | 3/2000 | Chopin et al. ............ 516/33 X |
| 6,221,296 B1 | * | 4/2001 | James et al. ................. 264/153 |
| 6,328,947 B1 | * | 12/2001 | Monden et al. .......... 502/350 X |
| 6,337,301 B1 | * | 1/2002 | Ohmori et al. ............. 502/350 |
| 6,352,586 B1 | * | 3/2002 | Lassmann ............... 106/447 X |
| 6,423,130 B2 | * | 7/2002 | Boinowitz et al. ........ 516/33 X |
| 6,500,415 B2 | * | 12/2002 | Ishii et al. ................. 424/59 X |
| 6,649,156 B1 | * | 11/2003 | Chane-Ching ................ 516/33 |
| 6,740,312 B2 | * | 5/2004 | Chopin et al. ................ 424/59 |
| 2003/0082122 A1 | * | 5/2003 | Chopin et al. ................ 424/63 |

FOREIGN PATENT DOCUMENTS

WO    WO97/10185    * 3/1997

* cited by examiner

Primary Examiner—Daniel S. Metzmaier
(74) Attorney, Agent, or Firm—Burns, Doane, Swecker & Mathis, L.L.P.

(57) ABSTRACT

An organic sol is disclosed comprising titanium oxide particles; an organic liquid phase and at least am amphiphilic compound selected among polyethylene phosphate alkyl ethers. In a first embodiment, the method for preparing said sol mixes said amphiphilic compound and the organic liquid phase, and disperses the titanium oxide particles in the resulting mixture. In a second embodiment, the method forms a mixture of titanium oxide and at least said amphiphilic compound, then disperses said mixture in said liquid phase. A solid compound comprising a mixture of titanium oxide particles and at least an amphiphilic compound selected among these mentioned above is also disclosed.

14 Claims, No Drawings

ORGANIC SOL AND SOLID COMPOUND BASED ON TITANIUM OXIDE AND AMPHIPHILIC COMPOUND AND PREPARATION METHODS

The present invention relates to an organic sol and a solid compound based on titanium oxide and an amphiphilic compound and their preparation processes.

Colloidal sol or dispersions of titanium oxide in organic media are known. However, the preparation processes of these sols are complex from an industrial point of view. A first class of processes uses compounds sensitive to water such as titanium alkoxides. Another class generally involves the preparation of an aqueous sol in the first instance and secondly bringing this aqueous sol into contact with an organic phase in order to transfer the titanium oxide into the organic phase. Such an operating method is not suitable for preparing sols in polar phases which are miscible with water. There is therefore a requirement for simpler processes which also provide access to sols with varying characteristics.

A subject of the present invention is to provide such processes and such organic sols.

For this purpose, the organic sol according to the invention is characterized in that it comprises titanium oxide particles; an organic liquid phase and at least one amphiphilic compound chosen from the polyoxyethylenated alkyl ether phosphates.

The invention also relates to a process for the preparation of such a sol which, according to a first variant, is characterized in that said amphiphilic compound and the organic liquid phase are mixed together, then the titanium oxide particles are dispersed in the mixture obtained. According to a second variant, the process is characterized in that a mixture of titanium oxide particles and at least one said amphiphilic compound are mixed together and said mixture is dispersed in the organic liquid phase.

The sols according to the invention have the advantage of being able to exist in a wide range of solvents, polar or non-polar solvents.

Other characteristics, details and advantages of the invention will appear more fully on reading the following description and the various concrete but non-limitative examples intended to illustrate it.

In the remainder of the description, the expression sol or colloidal dispersion of titanium oxide designates any system constituted by fine solid particles of colloidal dimensions based on titanium oxide suspended in a liquid phase, said types also being optionally able to contain residual quantities of linked or adsorbed ions such as for example chlorides, sulphates, nitrates, acetates, citrates, ammoniums or organic bases such as diethylamine. It should be noted that in such dispersions, the titanium may either be totally in the form of colloids or simultaneously in the form of ions and in the form of colloids.

The particles of the sol according to the invention can be based on titanium dioxide with a mainly anatase crystal structure. "Mainly" means that the content of the anatase titanium dioxide particles is higher than 50% by mass. Preferably, the particles have an anatase content greater than 80%. The degree of crystallization rate and the nature of the crystalline phase are measured by XR diffraction.

These particles can also be of rutile structure.

The average diameter of these particles in the sol is generally at most 250 nm, preferably at least 15 nm, even more preferentially between 20 and 70 nm. It is specified here that the average diameter of the particles or colloids must be understood as designating the average hydrodynamic diameter of the latter, and as determined by quasi-elastic diffusion of light according to the method described by Michael L. Mc Connell in the Journal Analytical Chemistry 53, no. 8, 1007 A, (1981).

The particles of the sol according to the invention generally have a BET specific surface area of at least 200 $m^2/g$, preferably at least 250 $m^2/g$.

By BET specific surface area is meant the specific surface area determined by nitrogen adsorption according to the ASTMD 3663–78 standard based on the BRUNAUER-EMMETT-TELLER method described in the periodical "The Journal of the American Society", 60, 309 (1938). In order to measure the specific surface area of the particles according to the invention, when they are in the form of a dispersion, it is essential to follow the measurement protocol which consists of eliminating the liquid phase from the dispersion then drying the particles under vacuum at a temperature of 150° C. for at least 4 hours.

According to two variants of the invention, the titanium oxide particles of the sol can comprise a coating. Before the following description of these two variants, it can be specified here that in both cases, the particles have an average diameter generally of at most 100 nm, preferably at least 25 nm, even more preferentially comprised between 50 and 70 nm. These coated particles also generally have a BET specific surface area of at least 70 $m^2/g$, preferably at least 100 $m^2/g$.

In the first or these variant, the titanium oxide particles are at least partially coated with a layer of at least one metallic or silicon oxide, hydroxide or oxyhydroxide. For this first variant, reference can be made to Patent Application EP-A-880564 the teaching of which relating to the description of the product and its method of preparation is incorporated here by way of reference. These metallic oxides, hydroxides or oxyhydroxides can in particular be chosen from $SiO_2$, $ZrO_2$, aluminium, zinc, titanium or tin oxides, hydroxides or oxyhydroxides in simple or mixed form. By mixed is understood a metallic compound based on at least two of the aforementioned elements (silicoaluminates, etc.).

In general, the ratio by weight of the metallic oxides, hydroxides or oxyhydroxides to the titanium dioxide is at most 60% by weight. This ratio is a function of the use for which the particles are intended. Preferably, when the particles are used in a cosmetic application, this ratio is 25%, even more preferentially at most 20%.

This quantity of metallic oxide, hydroxide or oxyhydroxide is measured on the particles in dispersion by X-ray fluorescence.

According to a particular embodiment of the invention, the particles are at least partially covered with a layer of silica and/or an aluminium oxide, hydroxide or oxyhydroxide in simple or mixed form.

According to another embodiment, the particles are covered with a layer of silica and aluminium hydroxide or oxyhydroxide with an $SiO_2$ content of 30% by weight and an $Al_2O_3$ content of 15% by weight with respect to the titanium dioxide.

According to more particular embodiment, the particles are covered with a layer of silica and aluminium hydroxide or oxyhydroxide with an $SiO_2$ content of 15% by weight and an $Al_2O_3$ content of 5% by weight with respect to the titanium dioxide.

According to the second of these variants, the titanium oxide particles are at least partially covered with a first layer of at least one compound of cerium and/or iron, and a second layer of least one metallic or silicon oxide, hydroxide or oxyhydroxide. For this second variant, reference can be made to Patent Application WO-A-98/01392 the teaching of which relating to the description of the product and its preparation method are incorporated here by way of reference.

The compounds present in the first aforementioned layer are precursors of cerium or iron oxide, i.e. they are thermally decomposable to cerium or iron oxide. They may be cerium or iron salts.

Particles covered with a cerium compound are preferred. The ratio by weight of the cerium compound(s) to the titanium dioxide is preferably at most 6% by weight, expressed in $CeO_2$. This ratio can be optimized as a function of the size of the particles. Thus, It has been observed that for particles of 25 nm diameter, the optimum cerium content was 5.5% by weight, expressed in $CeO_2$, with respect to the titanium dioxide, similarly for particles of 45 nm diameter, this content is 4.5%; for particles of 60 nm diameter, this content is 3%, and for particles of 80 nm diameter, this content is 2%.

The particles of this second variant are also at least partially covered with a second layer based on at least one metallic oxide, hydroxide or oxyhydroxide. The oxide is generally $SiO_2$, while the metallic hydroxide or oxyhydroxide can in particular be chosen from the aluminium, zinc, titanium or tin hydroxides or oxyhydroxides in simple or mixed form (as defined above).

In general, the ratio by weight of the metallic oxides, hydroxides or oxyhydroxides to the titanium dioxide is at most 60% by weight. This ratio is a function of the use for which the particles are intended. Preferably, when the particles are used in a cosmetic application, this ratio is at most 25%, even more preferentially at most 20%.

These quantities of metallic compounds, oxides, hydroxides or oxyhydroxides are measured on the particles in dispersion by X-ray fluorescence.

According to a particular embodiment, the particles are covered at least partially with a first layer of a compound of cerium and a second layer based on silica and/or an aluminium hydroxide or oxyhydroxide in simple or mixed form. The contents by weight can in this case be 15% of $SiO_2$ and 5% of $Al_2O_3$ with respect to the titanium dioxide. The second layer can also be based solely on silica with a content by weight of 30% of $SiO_2$.

The organic liquid phase of the sol according to the invention can be based on an organic liquid or a very varied mixture of organic liquids.

The organic solvent or liquid can be an inert cycloaliphatic or aliphatic hydrocarbon, or a mixture of the two, such as for example mineral spirits or naphtha which may also contain aromatic components. There can be mentioned for example hexane, heptane, octane, nonane, decane, cyclohexane, cyclopentane, cycloheptane and liquid naphthenes. The aromatic solvents such as benzene, toluene, ethybenzone and the xylenes are also suitable as well as petroleum fractions of ISOPAR or SOLVESSO type (trade marks registered by the company EXXON), in particular SOLVESSO 100 which mainly contains a mixture of methylethyl and trimethylbenzene, and SOLVESSO 150 which contains a mixture of alkyl benzenes, in particular dimethylethylbenzene and tetramethylbenzene.

Chlorinated hydrocarbons can also be used such as chloro or dichlorobenzene, chlorotoluene as well as aliphatic and cycloaliphatic ethers such as diisopropyl ether, dibutyl ether and aliphatic and cycloaliphatic ketones such as methylisobutylketone, diisobutylketone, mesityl oxide.

Ketones can also be used such as acetone, aldehydes, nitrogenous solvents such as acetonitrile, alcohols, acids and phenols.

Esters can also be envisaged. As esters which may be used there can in particular be mentioned those resulting from the reaction of acids with C1 to C8 alcohols and in particular secondary alcohol palmitates such as isopropanol. The acids from which these esters originate can be aliphatic carboxylic acids, aliphatic sulphonic acids, aliphatic phosphonic acids, alkylarylsulphonic acids and alkylarylphosphonic acids having approximately 10 to approximately 40 carbon atoms, either natural or synthetic. By way of example there can be mentioned the fatty acids of tallol, coconut oil, soya oil, tallow oil, linseed oil, oleic acid, linoleic acid, stearic acid and its isomers, pelargonic acid, capric acid, lauric acid, myristic acid, dodecylbenzenesulphonic acid, 2 ethyl hexanoic acid, naphthenic acid, hexoic acid, toluenesulphonic acid, toluene-phosphonic acid, lauryl-sulphonic acid, lauryl-phosphonic acid, palmityl-sulphonic acid and palmityl-phosphonic acid.

According to a particularly useful characteristic of the sol according to the invention, the organic liquid phase is based on a polar solvent or a mixture of polar solvents. By polar solvent is meant those having a dielectric constant $\in_r$ greater than 5, as defined in particular in the publication "Solvents and Solvent Effects in Organic Chemistry", C. Reichardt, VCH, 1988. This polar solvent can be chosen from halogenated solvents such as dichloromethane; esters of ethyl acetate, isopropyl palmitate, methoxy-propyl acetate type; alcohols such as ethanol, butanol or isopropanol; polyols such as propane diol, butane diol or diethylene glycol; ketones such as cyclohexanone or 1-methylpyrrolidin-2-one.

According to an important characteristic of the invention, the sol further comprises an amphiphilic compound. Without wishing to be bound by one explanation, it can be considered that this amphiphilic compound is adsorbed on or in electrostatic interaction with the titanium oxide particles or also complexed with the latter.

This compound is chosen from the polyoxyethylenated alkyl ether phosphates. The polyoxyethylenated alkyl ether phosphates of the following formula are meant here:

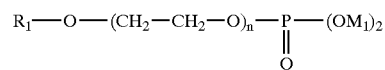

or also the polyoxyethylenated dialkoyl phosphates of formula:

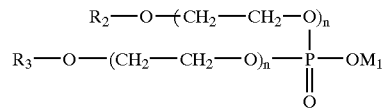

in which $R_1$, $R_2$, $R_3$, identical or different, represent a linear or branched alkyl radical, in particular with 2 to 20 carbon atoms; a phenyl radical; an alkylaryl radical, more particularly an alkylphenyl radical, in particular with an alkyl chain with 8 to 12 carbon atoms; an arylalkyl radical, more particularly a phenylaryl radical; n the number of ethylene oxide being able to vary from 2 to 12 for example; M1 represents a hydrogen, sodium or potassium atom. The $R_3$ radical can in particular be a hexyl, octyl, decyl, dodecyl, oleyl, nonylphenyl radical.

As an example of this type of amphiphilic compound there can be mentioned those marketed under the brand names Lubrophos® and Rhodafac® and in particular the products below:

the poly-oxy-ethylene-alkyl (C8–C10) ether phosphates Rhodafac® RA 600 the polyoxyethylene tri-decyl ether phosphate Rhodafac® RS 710 or RS 410 the poly-oxy-ethylene oleoketyl ether phosphate Rhodafac® PA 35 the poly-oxy-ethylene nonylphenyl ether phosphate Rhodafac® PA 17 the poly-oxy-ethylene nonyl(branched) other phosphate Rhodafac® RE 610

The amphiphilic compound is chosen as a function of the nature of the organic liquid phase. More specifically, this choice is made by adapting the hydrophilic/lipophilic equilibrium of the amphiphilic compound to the hydrophilic/lipophilic character of the organic phase. In other words, the more polar the solvent contained in the organic phase, the more hydrophilic the amphiphilic compound will be.

The proportion of amphiphilic compound with respect to the titanium oxide is generally comprises between 2 and 10 molecules per nm$^2$ of titanium oxide surface area, assuming a surface area comprised between 10 and 80 Å$^2$ per complexing head of titanium cation.

The sol according to the invention have a concentration of titanium compound which can reach 40% expressed by weight of TiO$_2$ with respect to the total weight of the dispersion.

The organic sole produced in this way have excellent stability. No settlement is observed after several months.

The present invention also relates to a solid compound which is characterized in that it comprises a mixture of titanium oxide particles and at least one amphiphilic compound chosen from those described above.

This solid compound is presented either in the form of a paste or in the form of a powder. The titanium oxide is presented in this solid compound in the form of aggregated elementary crystallites, the average size of the aggregates ranging from 20 to 100 nm. The sold compound has the property of being redispersible, i.e. being able to produce a sol according to the invention and as described above when it is suspended in an organic liquid phase.

The titanium oxide particles of the solid compound according to the invention can comprise a coating which is at least partial in the form of a layer of at east one silicon or metallic oxide, hydroxide or oxyhydroxide or also in the form of a first layer of at least one compound of cerium and/or iron and a second layer of at least one silicon or metallic oxide, hydroxide or oxyhydroxide.

What was described previously regarding the particles of the sol also applies here for the solid compound, The preparation processes for the solid compound and the sol according to the invention will now be described.

As starting product, any titanium oxide is used which is capable of producing a sol when it is dispersed in a liquid phase and in particular any titanium oxide capable of being in the form described above regarding the solid compound.

There follows the description of and the preparation process for the titanium oxide particles which are particularly suitable as starting products for preparing the sol and the solid compound according to the invention.

The starting products are based on titanium dioxide with a mainly anatase crystal structure as defined previously.

These starting anatase titanium dioxide particles can be of a size of at most 100 nm, preferably at least 15 nm, yet more preferentially comprised between 20 and 70 nm. This diameter is measured by transmission electron microscopy (TEM). Their BET specific surface area is generally at least 200 m$^2$/g, preferably at least 250 m$^2$/g. This BET specific surface area is measured as defined previously.

The starting particles also have a density of the order of 2.5. By "of the order of" is meant that the density is 2.5±0.2. This density is given by the following formula:

$$\text{density} = \frac{1}{(1/\rho) + Vi}.$$

in which:

ρ is the density of the anatase, i.e. 3.8,

VI is the volume provided by the intraparticle pores, measured by the BJH method. By volume measured by the BJH method is meant the volume measured using the BARRETT-JOYNER-HELENDA method described in an article in the publication "Techniques de l'Ingénleur" and entitled "Texture des solides poreux ou divsés", p. 3645–1 to 3645–13.

In order to measure the volume provided by the intraparticle pores of the particles according to the invention, when they are in the form of a dispersion, it is essential to follow the measurement protocol which consists of eliminating the liquid phase of the dispersion then drying the particles under vacuum at a temperature of 150° C. for at least 4 hours.

Particles as described above can be obtained by hydrolysis of at least one titanium compound A in the presence of at least one compound B chosen from:

(i) the acids having;

either a carboxyl group and at least two hydroxyl and/or amine groups.

or at least two carboxyl groups and at least one hydroxyl and/or amine group, (ii) the organic phosphoric adds of the following formulae:

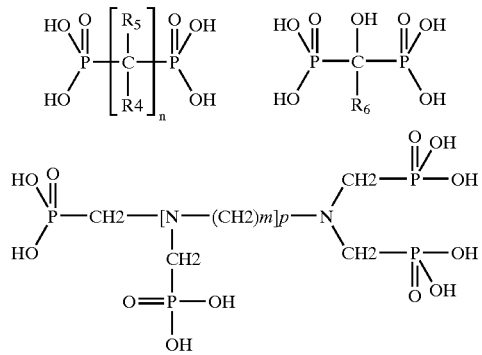

in which n and m are integers comprised between 1 and 6, p is an integer comprised between 0 and 5, $R_4$, $R_5$ and $R_6$ identical or different represent a hydroxyl, amino, aralkyl, aryl, alkyl group or hydrogen, (iii) the compounds capable of releasing sulphate ions in an acid medium, (iv) the salts of the acids described above, and in the presence of anatase titanium dioxide seeds.

The starting solution, intended to be hydrolyzed, is preferably totally aqueous; another solvent, such as an alcohol, can optionally be added provided that the titanium compound A and compound B used are substantially soluble in this mixture.

As regards the titanium compound A, a compound chosen from titanium halides, oxyhalides, alkoxides, sulphates and more particularly synthetic sulphates is generally used.

By synthetic sulphates is meant solutions of titanyl sulphates produced by ion exchange from very pure titanium chloride solutions or by reacting sulphuric acid with a titanium alkoxide.

The preparation is preferably carried out with titanium compounds of the titanium halide or oxyhalide type. The titanium halides or oxyhalides which are more particularly used in the present invention are titanium fluorides, chlorides, bromides and iodides (respectively oxyfluorides, oxychlorides, oxybromides and oxyiodides).

According to particularly preferred method, the titanium compound is titanium oxychloride $TiOCl_2$.

The quantity of the titanium compound A present in the solution to be hydrolyzed is not critical.

The initial solution further contains at least one compound B as defined previously. As non-limitative example of compounds B falling within the scope of the present invention, there can be mentioned in particular:

hydroxypolycarboxylic acids, and more particularly hydroxydi- or hydroxytricarboxylic acids such as citric acid, maleic acid and tartaric acid, (polyhydroxy)monocarboxylic acids, such as for example glucoheptonic acid and gluconic acid, poly(hydroxycarboxylic) acids, such as for example tartaric acid dicarboxylic monoacids and their corresponding amides, such as for example aspartic acid, asparagine and glutamic acid, monocarboxylic aminoacids, hydroxylated or non-hydroxylated, such as for example lysine, serine and threonine, methylene aminotriphosphonate, methylene ethylenediaminotetraphosphonate, methylene triethylenetetraaminohexaphosphonate, methylene tetraethylenepentaaminoheptaphosphonate, methylene pentaethylenehexaaminooctaphosphonate, methylene diphosphonate; 1,1' ethylene diphosphonate; 1,2 ethylene diphosphonate; 1,1' propylene diphosphonate; 1,3 propylene diphosphonate; 1,6 hexamethylene diphosphonate; 2,4 dihydroxypentamethylene 2,4 disphosphonate; 2,6 dihydroxyhexmethylene 2,5 diphosphonate; 2,3 dihydroxybutylene 2,3 diphosphonate; 1 hydroxybenzyl 1,1' diphosphonate; 1 aminoethylene 1-1' diphosphonate; hydroxymethylene diphosphonate; 1 hydroxyethylene 1,1' diphosphonate; 1 hydroxypropylene 1-1' diphosphonate; 1 hydroxybutylene 1-1' diphosphonate; 1 hydroxyhexamethylene 1,1' diphosphonate.

As already Indicated, it is also possible to use all the salts of the aforementioned acids as compound B. In particular, these salts are either alkaline salts and more particularly sodium salts, or ammonium salts.

These compounds can also be chosen from sulphuric acid and ammonium and in particular potassium sulphates.

Preferably, the compounds B as defined above are hydrocarbon-comprising compounds of aliphatic type. In this case, the length of the main hydrocarbon-comprising chain preferably does not exceed 15 carbon atoms, and more preferentially 10 carbon atoms. The preferred compound B is citric acid.

The quantity of compound B is not critical. In general, the molar concentration of compound B with respect to that of titanium compound A is comprised between 0.2 and 10% and preferably between 1 and 5%.

Finally, the starting solution comprises titanium dioxide seeds. The preferred specific characteristics of these seeds and their use are given below.

Thus, the titanium dioxide seeds used in the present invention firstly are of a size of less than 8 nm, measured by X-ray diffraction. Preferably, titanium dioxide seeds are used having a size comprised between 3 and 5 nm.

Next, the ratio by weight of titanium dioxide present in the titanium seeds present in the hydrolysis medium before introducing the seeds—i.e. provided by titanium compound A—and expressed in $TiO_2$ is comprised between 0.01 and 3%. This ratio can preferentially be comprised between 0.05 and 1.5%. The combination of these two conditions with respect to the seeds (size and ratio by weight) combined with the process described previously allows precise control over the final size of the titanium dioxide particles, a level of seeds being associated with a particle size. Particles can be obtained in this way with a diameter which varies between 20 and 100 nm.

Titanium dioxide seeds are used in anatase form in order to induce the precipitation of the titanium dioxide in anatase form. Generally, as a result of their small size, these seeds are in a poorly crystallized anatase form. These seeds usually take the form of an aqueous suspension constituted by titanium dioxide. They can generally be obtained in a known manner by a process for neutralizing a titanium salt by a base.

The following stage consists in hydrolyzing the starting solution by any means known to a person skilled in the art and in general by heating. In the latter case, hydrolysis can preferably be carried out at a temperature greater than or equal to 70° C. It is also possible initially to operate at a temperature lower than the medium's boiling point then maintain the hydrolysis medium level at the boiling point.

Once hydrolysis is achieved, the titanium dioxide particles obtained are recovered by separating the precipitated solid from the mother liquors. They can be redispersed in a liquid medium, preferably acid or basic, for example in water, in order to obtain a dispersion of titanium dioxide.

According to a variant of the process, after recovering the particles obtained following hydrolysis and before they are redispersed, the particles can be neutralized and/or subjected to at least one washing operation. The particles can be recovered for example by centrifuging the solution resulting from hydrolysis, they are then neutralized by a base, for example an ammonium hydroxide or soda solution. They can be washed by redispersing them in an aqueous solution then the particles are separated from the aqueous washing phase. After optionally one or more other washing operations of the same type, the particles are redispersed in a liquid, for example water, which can preferably be acid or basic.

As regards titanium oxide particles in rule form, these can be obtained by hydrolysis of a titanium compound chosen from the titanium halides, oxyhalides and alkoxides.

Titanium particles can be used in solid form by simple evaporation or by drying at a temperature of at most 120° C. of the aforementioned dispersion, i.e. that obtained after hydrolysis, separation from the hydrolysis medium and replacing in a liquid phase. This temperature is preferably comprised between 30 and 80° C.

As regards the preparation of the titanium oxide particles according to the two variants described above, i.e. those in which the particles comprise a coating, the process is carried out according to the contents of the aforementioned Patent Applications EP-A-880584 and WO-A98/01392. It can be recalled here, in the case of the first variant, that the process consists of precipitating at least one metallic oxide, hydroxide or oxyhydroxide on the surface of the titanium dioxide particles. This precipitation can be achieved by introducing into a dispersion of precursors of titanium dioxide particles metallic oxides, hydroxides or oxyhydroxides generally in the form of aqueous solutions of salts, then modifying the pH in order to obtain the precipitation of these oxides, hydroxides or oxyhydroxides on the titanium dioxide particles.

In the case of the second variant, the process consists of precipitating at least one compound of cerium and/or iron on the surface of the titanium dioxide particles then of precipitating at least one metallic oxide, hydroxide or oxyhydroxide on the surface of the particles obtained.

These precipitations can also be achieved by introducing into a dispersion of precursors of titanium dioxide particles compounds of cerium and/or iron, metallic oxides, hydroxides or oxyhydroxides generally in the form of aqueous solutions of salts, then modifying the pH in order to obtain the precipitation of these compounds, oxides, hydroxides or oxyhydroxide on the titanium dioxide particles.

In general and for the two variants, this precipitation is carried out at a temperature of at least 50° C.

The preparation process for the sol according to the invention can be implemented according to a first variant in this variant the aforementioned amphiphilic compound and the organic liquid phase are mixed together, then the titanium oxide particles are dispersed in the mixture obtained. It should be noted that it is possible either to introduce the solid particles into the amphiphilic compound/organic phase mixture or to pour this mixture onto the titanium oxide particles. Once the particles, the amphiphilic compound and the organic phase have been brought into contact, agitation is carried out until a stable colloidal dispersion is obtained.

There is a second variant of the process. In this case, a mixture of titanium oxide and at least one aforementioned amphiphilic compound is formed. This mixture can be achieved using any known mechanical means such as mixing in order to obtain a homogeneous paste. In this way, a solid compound is obtained as defined above. Said mixture is then dispersed in the organic liquid phase.

A third variant will now be described which is more particularly suitable for the preparation of a sol in a polar organic phase.

This variant, for the preparation of a sol according to the invention in an organic liquid phase (a) includes a first stage in which a dispersion is formed comprising titanium oxide particles and at least one amphiphilic compound of the aforementioned type in an organic liquid phase (b) based on a solvent with lower polarity than that of the solvent of the organic liquid phase (a). On formation of this dispersion, segregation can be observed due to water which may be present in the starting hydrated titanium oxide. In this case, the segregated water is separated from the rest of the dispersion.

In a second stage, the solid phase of the dispersion is separated from its liquid phase by). This separation can be carried out by any suitable technique. The separation can thus be carried out by flocculation by a third solvent or also by distillation or evaporation. Following this separation, a solid phase is obtained which can be dried and which takes the form, depending on the extent of drying, either of a powder or of a paste and which constitutes a solid compound according to the invention. In a last stage, the phase or the solid compound obtained in this way is redispersed in the organic phase (a) in order to obtain the sought sol.

The dispersions of titanium oxide particles in the organic phase can be subjected to an ultrafiltration treatment in order to improve their stability if necessary.

Finally, it should be noted that the sols obtained can be subjected to a dehydration post-treatment by passing them over a solid desiccant for example.

The sols according to the invention can be used in all the applications where titanium is used for its photocatalytic properties. In this case, the titanium oxide particles do not comprise any coating of the type described above.

The sols based on titanium oxide particles according to the invention and in particular those comprising particles with a coating of this type can be used as anti-UV agents in the preparation of formulations for cosmetics, varnishes, paints and plastics.

Non-limitative examples will now be given.

EXAMPLE 1-A

This example and the following relate to the preparation of a colloidal dispersion In an isopar medium. The titanium oxide particles are first prepared as follows.

The following are added successively to 394.7 g of a titanium oxychloride solution at 1.9 mol/kg:

42.02 g of 36% hydrochloric acid, 4.73 g of citric acid, 547.1 g of purified water, 73.84 g of a suspension containing 1.06% by weight of anatase seeds.

The mixture is taken to boiling and maintained at boiling point for 3 hours. The solution is left to settle and the supernatant is siphoned out, followed by redispersing with one volume of demineralize water with one volume of water in order to obtain a dry extract of 20% by weight. In this way a perfectly stable sol is obtained. The size of the colloids is 22 nm.

11.2 g of ester phosphate Rhodafac RS 410 marketed by Rhodia is then first dissolved in 70 g of isopar L at ambient temperature and under agitation. 10 g of $TiO_2$ powder is then introduced progressively into this mixture. This $TiO_2$ powder was obtained by drying the colloidal dispersion of $TiO_2$ oxide previously described at 50° C. and contains 77% of $TiO_2$. The reaction mixture is completed with isopar to reach a total mass (amphiphilic compound+$TiO_2$ powder+ isopar) equal to 100 g, then left under agitation until a stable colloidal dispersion is obtained. A particle size is observed which is substantially identical to the size of the particles present in the initial aqueous colloidal dispersion.

EXAMPLE 1-B 26 g of $TiO_2$ powder obtained by drying the colloidal dispersion described in Example 1-a at 50° C. is introduced. 29.9 g of ester phosphate RS 410 and $CH_2Cl_2$ is added to reach 336 g. Agitation is carried out overnight until a dispersion is obtained.

An aliquot of 168 g of the dispersion is evaporated in a rotary evaporator at 30° C. under vacuum obtained by a water suction pump. The powder obtained in this way is redispersed in an equivalent volume of isopar A dispersion in isopar is obtained which is stable over time.

EXAMPLE 2-A

This example and the next example relate to the preparation of a colloidal dispersion in a xylene medium.

15.6 g of ester phosphate Rhodafac RS 710 marketed by Rhodia is first dissolved in 60 g of xylene at ambient temperature and under agitation. 10 g of $TiO_2$ powder obtained by drying the colloidal dispersion of $TiO_2$ previously described at 50° C. is progressively introduced into this mixture to which xylene is added at ambient temperature to a total mass of 100 g. The reaction mixture is left under agitation until a stable colloidal dispersion is obtained.

A particle size is observed which is substantially identical to the size of the particles present in the initial aqueous colloidal dispersion.

EXAMPLE 2-B 28 g of TiO2 powder obtained by drying the colloidal dispersion described in Example 1-a at 50° C. is introduced. 29.9 g of ester phosphate RS 410 is added and CH2Cl2 solvent is added to reach 338 g. Agitation is carried out overnight until a dispersion is obtained.

An aliquot of 168 g of dispersion is evaporated in a rotary evaporator at 30° C. under vacuum obtained by a water-jet aspirator pump. The paste obtained in this way is redispersed in an equivalent volume of xylene. A dispersion in xylene is obtained which is stable over time.

EXAMPLE 3

This example relates to a colloidal dispersion in an ethyl acetate medium.

1.93 g of ester phosphate Rhodafac® RS 710 marketed by Rhodia is first dissolved in 15 g of xylene at ambient temperature and under agitation. 2 g of TiO2 powder obtained by drying the colloidal dispersion of TiO2 oxide previously described at 50° C. is added progressively and xylene is added at ambient temperature to reach 20 g. Agitation is carried out until a stable colloidal dispersion to obtained.

5 g of the colloidal dispersion obtained in this way is evaporated at ambient temperature under a ventilated hood. The paste obtained in this way is redispersed in 4.11 g of ethyl acetate. After agitation, a colloidal dispersion is obtained which is stable over time. A particle size of 24 nm is observed, which is substantially identical to the size of the particles present in the initial aqueous colloidal dispersion.

EXAMPLE 4

This example relates to a colloidal dispersion in a butanol medium.

0.77 g of ester phosphate Rhodafac® RS 710 marketed by Rhodia is first dissolved in 15 g of xylene at ambient temperature and under agitation. 2 g of TiO2 powder obtained by drying the colloidal dispersion of TiO2 oxide previously described at 50° C. is introduced and xylene is added at ambient temperature in order to reach a total mass of 20 g. Agitation is carried out until a stable colloidal dispersion is obtained.

5 g of the colloidal dispersion obtained in this way is evaporated at ambient temperature under a ventilated hood. The paste obtained in this way is redispersed in 4.35 g of butanol. After agitation, a colloidal dispersion is obtained which is stable over time. A particle size of 28 nm is observed.

EXAMPLE 5

This example relates to a colloidal dispersion in an ethanol medium 1.93 g of ester phosphate RS 710 marketed by Rhodia is first dissolved in 15 g of xylene at ambient temperature and under agitation. 2 g of TiO2 powder obtained by drying the colloidal dispersion of TiO2 oxide previously described at 50° C. is added progressively and xylene is added at ambient temperature to read 20 g. Agitation is carried out until a stable colloidal dispersion is obtained.

5 g of the colloidal dispersion obtained in this way is evaporated at ambient temperature under a ventilated hood. The paste obtained in this way it redispersed in 4.11 g of absolute ethanol. After agitation, a colloidal dispersion is obtained which is stable over time. A particle size of 23 nm is observed.

EXAMPLE 6

This example relates to a colloidal dispersion of TiO2 coated with Al2O3 and SiO2 in isopar, A colloidal dispersion of TiO2 nanoparticles is used the surface of which has been treated according to the operating method described in Example 2 of Patent Application EP-A-80584, the starting titanium oxide particles having been obtained according to Example 1 of said Application and by adding to the titanium oxychloride solution 17.04 g of a suspension containing 1.06% by weight of anatase seeds having a size comprised between 5 and 6 nm. The colloidal dispersion has a dry extract of approx. 35%, colloids 60 nm in size. The composition of the surface coating is 15% SiO2–5% Al2O3, the pH of the dispersion is 8.7.

This colloidal dispersion is evaporated overnight at 50° C. in a ventilated oven.

A powder is obtained with 85.5% oxide.

A solution is prepared with 12.5% by weight of Rhodafac RS 410 in isopar.

18 g of the 125% isopar solution is added to 2 g of the dried powder obtained as described previously. A colloidal dispersion is then obtained which is stable over time.

EXAMPLE 7

This example relates to a colloidal dispersion of TiO2 coated with Al2O3 and SiO2 in isopropyl palmitate.

0.44 g of Rhodafac RS 410 and 18 g of isopropyl palmitate are added to 2.34 g of TiO2 powder surface treated as described previously in Example 6. After agitation at ambient temperature, a colloidal dispersion is obtained which is stable over time.

EXAMPLE 8

This example relates to a colloidal dispersion of TiO2 coated with Al2O3 and SiO2 in isopropyl palmitate and with a high concentration of titanium oxide.

112 g of Rhodafac RS 410 is solubilized in 80 g of isopropyl palmitate. 60 g of TiO2/Al2O3-SiO2 powder produced as described previously in Example 6 is then added slowly, under agitation. After agitation at ambient temperature for 3 days, a dispersion is obtained. After dilution in isopropyl palmitate, a size of the order of 63 nm is determined, which is substantially identical to the size of the nanoparticles of the initial dispersion.

EXAMPLE 9

This example relates to a colloidal dispersion of TiO2 coated with two layers, one based on CeO2, the other based on Al2O3 and SiO2 in isopropyl palmitate.

The colloidal dispersion of nanoparticles of TiO2 surface treated according to the operating method described in Example 2 of WO-A-98/01392, the starting titanium oxide particles having been obtained according to Example 1 of said Application and by adding to the titanium oxychloride solution 11.36 g of a suspension containing 1.06% by weight of anatase seeds of a size comprised between 5 and 6 nm. This dispersion has a dry extract of approximately 23%, colloids 45 nm in size. The composition of the surface treatment is 15% SiO2–5% Al2O3–5% CeO12, the pH of the dispersion 155.5.

This colloidal dispersion is evaporated overnight at 50° C. in a ventilated oven.

A power is obtained with 85.3% oxide.

11.2 g of Rhodafac RS 410 is solubilized in 80 g of isopropyl palmitate, 60 g of TiO2Al2O3-SiO2-CeO2 powder produced as described previously is added slowly and under agitation. After agitation at ambient temperature for 3 days, a dispersion is obtained which is stable over time. By granulometric analysis by dilution in isopropyl palmitate, a size of the order of 72 nm is determined, which is substantially identical to the size of the nanoparticles of the initial dispersion.

What is claimed is:

1. Process for the preparation of an organic sol, comprising:

titanium oxide particles;
   an organic liquid phase;
   at least one amphiphilic compound having a formulae:

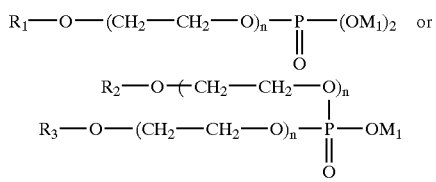

wherein,
   $R_1$, $R_2$, and $R_3$ are a linear or branched alkyl group, a phenyl group, an alkylaryl group or an arylalkyl group;
   n represents the number of ethylene oxide units and wherein n is from two to twelve; and
   M1 represents a hydrogen, sodium or potassium atom, the process comprising the following steps:
   a) preparing, as starting product, titanium dioxide particles by hydrolysis of at least one titanium compound A in the presence of at least one compound B selected from the group consisting of:
      (i) acids which have:
         either a carboxyl group and at least two hydroxyl and/or amine groups,
         or at least two carboxyl groups and at least one hydroxyl and/or amine group,
      (ii) organic phosphoric acids of the following formulas:

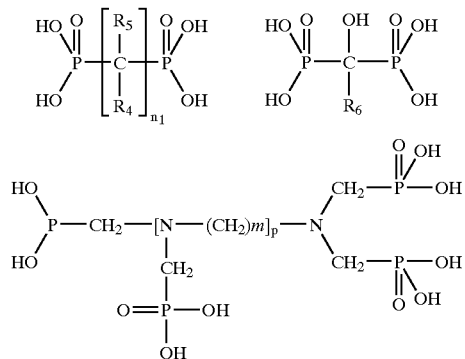

in which $n_1$ and m are integers between 1 and 6, p is an integer between 0 and 5, $R_4$, $R_5$ and $R_6$ identical or different represent a hydroxyl, amino, aralkyl, aryl, alkyl group or hydrogen group,
      (iii) compounds capable of releasing sulphate ions in an acid medium,
      (iv) salts of the acids described above and in the presence of anatase titanium dioxide seeds;
   b) optionally at least partially covering the particles by a layer of at least one of a silicon oxide, hydroxide or oxyhydroxide or a metallic oxide, hydroxide or oxyhydroxide; and
   c) mixing the amphiphilic compound and the organic liquid phase together, then dispersing the titanium oxide particles in the mixture obtained, or forming a mixture of titanium oxide particles and at least one of the aforementioned amphiphilic compounds, then dispersing said mixture in the liquid phase.

2. Process according to claim 1, wherein the titanium oxide particles are at least partially covered:
   by a first layer of at least one cerium and/or iron compound, and
   by a second layer of at least one silicon oxide, hydroxide or oxyhydroxide or metallic oxide, hydroxide or oxyhydroxide.

3. Process according to claim 2, wherein the first aforementioned layer is based on at least one cerium compound with a content such that a ratio by weight of the cerium compound, expressed in CeO2, to the titanium dioxide is at most 6% by weight.

4. Process according to claim 1, wherein the titanium oxide particles have a BET specific surface area of at least 70 $m^2/g$.

5. Process according to claim 1, wherein a ratio by weight of the silicon oxide(s), hydroxide(s) or oxyhydroxide(s) or metallic oxide(s), hydroxide(s) or oxyhydroxide(s) to titanium dioxide is at most 60% by weight.

6. Process according to claim 1, wherein the titanium oxide particles are at least partially covered by at least one layer based on silica oxide, hydroxide or oxyhydroxide and/or aluminum oxide, hydroxide or oxyhydroxide.

7. Process according to claim 1, wherein the organic liquid phase is based on a polar solvent.

8. Process according to claim 1, wherein the organic phase comprises a polar solvent selected from the group consisting of halogenated solvents, esters, and alcohols.

9. Process according to claim 1, wherein the organic sol comprises an organic liquid phase (a), the process comprising:
   forming a dispersion comprising the titanium oxide particles, and at least one of the amphiphilic compounds in an organic liquid phase (b) based on a solvent with a lower polarity than that of the organic liquid phase (a);
   separating a solid phase from the liquid phase (b); and
   dispersing the solid phase obtained in this way in the organic phase (a).

10. Process according to claim 1, comprising, as the starting product, titanium dioxide particles which were obtained by the hydrolysis process and in which the anatase titanium dioxide seeds are of a size no greater than 8 nm and are present in ratio by weight expressed in $TiO_2$ present in the seeds/titanium present before the introduction of the seeds into the hydrolysis medium, expressed in $TiO_2$ comprised between 0.01% and 3%.

11. Process according to claim 1, comprising, as the starting product, titanium dioxide particles which were obtained by the aforementioned hydrolysis process and in which the titanium compound A is titanium oxychloride.

12. Process according to claim 1, comprising, as the starting product, titanium dioxide particles which were obtained by the aforementioned hydrolysis process and in which compound B is citric acid.

13. Process according to claim 1, comprising, as the starting product, titanium dioxide particles which were obtained by a process comprising the aforementioned hydrolysis and in which precipitate formed is separated from hydrolysis medium then redispersed in water resulting in a dispersion of titanium oxide in water and where said dispersion is dried at a temperature no greater than 120° C.

14. Process according to claim 1, wherein the organic sol is subjected to an ultrafiltration treatment.

* * * * *